US00PP15935P2

(12) United States Plant Patent
van Delft

(10) Patent No.: US PP15,935 P2
(45) Date of Patent: Aug. 30, 2005

(54) ***CARYOPTERIS* PLANT NAMED 'SUMMER SORBET'**

(50) Latin Name: *Caryopteris×clandonensis*
Varietal Denomination: Summer Sorbet

(75) Inventor: Peter van Delft, Marldon Paignton (GB)

(73) Assignee: Witteman & Company, Hillegom (NL)

( * ) Notice: Subject to any disclaimer, the term of this patent is extended or adjusted under 35 U.S.C. 154(b) by 27 days.

(21) Appl. No.: 10/878,422

(22) Filed: Jun. 28, 2004

(51) Int. Cl.[7] ..... A01H 5/00
(52) U.S. Cl. ..... Plt./263

(58) Field of Search ..... Plt./263

(56) References Cited

PUBLICATIONS

UPOV–ROM GTITM Computer Database 2004/04, GTI Jouve Retrieval Software, Citation for 'Summer Sorbet'.*

* cited by examiner

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Caryopteris* plant named 'Summer Sorbet', characterized by its compact and mounded plant habit; freely branching growth habit; and green and yellow variegated leaves.

1 Drawing Sheet

Botanical classification/cultivar designation: *Caryopteris×clandonensis* cultivar Summer Sorbet.

BACKGROUND OF THE INVENTION

The present Invention relates to a new and distinct cultivar of *Caryopteris* plant, botanically known as *Caryopteris× clandonensis,* and hereinafter referred to by the name 'Summer Sorbet'.

The new *Caryopteris* is a naturally-occurring whole plant mutation of the *Caryopteris×clandonensis* cultivar Kew Blue, not patented. The new *Caryopteris* was discovered and selected by the Inventor as a single plant within a population of plants of the cultivar Kew Blue a controlled environment in Marldon Paignton, United Kingdom in 2001.

Asexual reproduction of the new cultivar by softwood cuttings at Marldon Paignton, United Kingdom since 2001, has shown that the unique features of this new *Caryopteris* are stable and reproduced true to type in successive generations of asexual reproduction.

SUMMARY OF THE INVENTION

The following traits have been repeatedly observed and are determined to be the unique characteristics of 'Summer Sorbet'. These characteristics in combination distinguish 'Summer Sorbet' as a new and distinct cultivar:

1. Compact and mounded plant habit.
2. Freely branching growth habit.
3. Green and yellow variegated leaves.

Plants of the new *Caryopteris* are most similar to plants of its parent, the cultivar Kew Blue. Plants of the new *Caryopteris* differ primarily from plants of the cultivar Kew Blue in foliage coloration as plants of the cultivar Kew Blue have solid green-colored leaves.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical plant of 'Summer Sorbet' grown in a container.

The photograph at the bottom of the sheet is a close-up view of typical leaves of 'Summer Sorbet'.

Flower and foliage colors in the photographs may differ slightly from the color values cited in the detailed botanical description which accurately describe the colors of the new *Caryopteris.*

DETAILED BOTANICAL DESCRIPTION

The cultivar Summer Sorbet has not been observed under all possible environmental conditions. The phenotype may vary somewhat with variations in environment such as temperature and light intensity, without, however, any variance in genotype. The aforementioned photographs and following observations and measurements describe plants grown in 19-cm containers in Boskoop, The Netherlands, under commercial practice in an outdoor nursery during the early spring. Plants used for the photographs and description were about two years old. During the production of the plants, day temperatures ranged from 5 to 18° C. and night temperatures ranged from about 0 to 8° C. In the following description, color references are made to The Royal Horticultural Society Colour Chart, 2001 Edition, except where general terms of ordinary dictionary significance are used.

Botanical classification: *Caryopteris×clandonensis* cultivar Summer Sorbet.

Parentage: Naturally-occurring whole plant mutation of the *Caryopteris×clandonensis* cultivar Kew Blue, not patented.

Propagation:

*Type cutting.*—Softwood cuttings.

*Time to initiate roots.*—About 50 days at 25° C.

*Time to develop roots.*—About 90 days at 22° C.

*Root description.*—Fine; moderately branching.

Plant description:

*General appearance.*—Deciduous shrub. Compact and mounded plant habit; flattened globular.

*Growth and branching habit.*—Freely branching; about nine lateral branches per plant. Pinching, that is, removal of the terminal apices, enhances branching potential. Moderately vigorous.

*Plant height.*—About 22 cm.

*Plant diameter or spread.*—About 23 cm.

*Lateral branch description.*—Length: About 19 cm. Diameter: About 3 mm. Internode length: About 3.5 cm. Texture: Smooth, glabrous. Color: Mottled, 199A and N199B.

*Foliage description.*—Arrangement: Opposite, simple. Length: About 3.2 cm. Width: About 1.7 cm. Shape: Oval to elliptic. Apex: Obtuse. Base: Attenuate. Margin: Entire to sparsely serrate. Texture, upper and lower surfaces: Smooth, glabrous. Venation pattern: Pinnate. Fragrance: When rubbed, strong, spicy. Color: Developing foliage, upper surface: Center, 143C to 144A; towards the margins, between 1A and 3A. Developing foliage, lower surface: Center, between 144C to 144D and N144D; towards the margins, 3B. Fully expanded foliage, upper surface: Center, 143C; towards the margins, between 1A and 3A. Fully expanded foliage, lower surface: Center, 144B; towards the margins, 1A. Venation, upper and lower surfaces: Same as lamina. Petiole: Length: About 8 mm. Diameter: About 1 mm. Color, upper and lower surfaces: 144B.

Flower description: Flower development has not been observed on plants of the new *Caryopteris.*

Disease/pest resistance: Plants of the new *Caryopteris* have not been observed to be resistant to pathogens and pests common to *Caryopteris.*

Temperature tolerance: Plants of the new *Caryopteris* have been observed to tolerate temperatures from −10 to 35° C.

It is claimed:

1. A new and distinct cultivar of *Caryopteris* plant named 'Summer Sorbet', as illustrated and described.

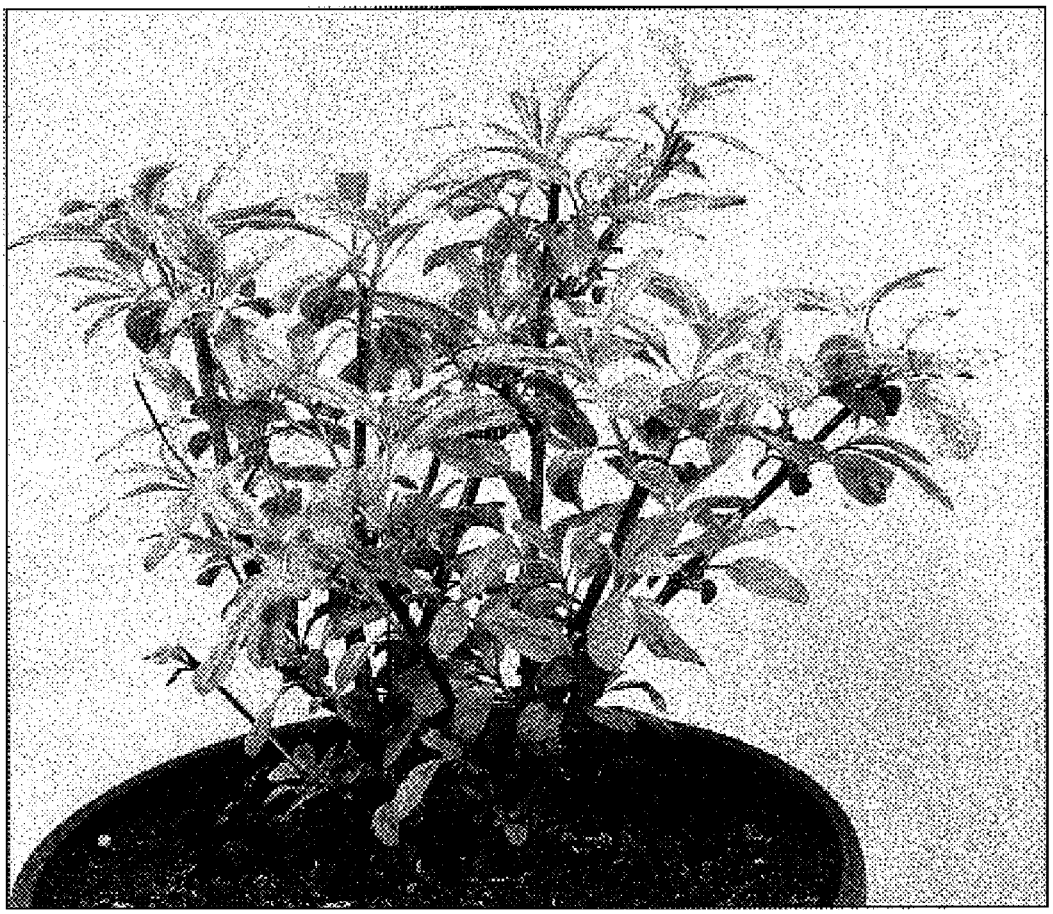
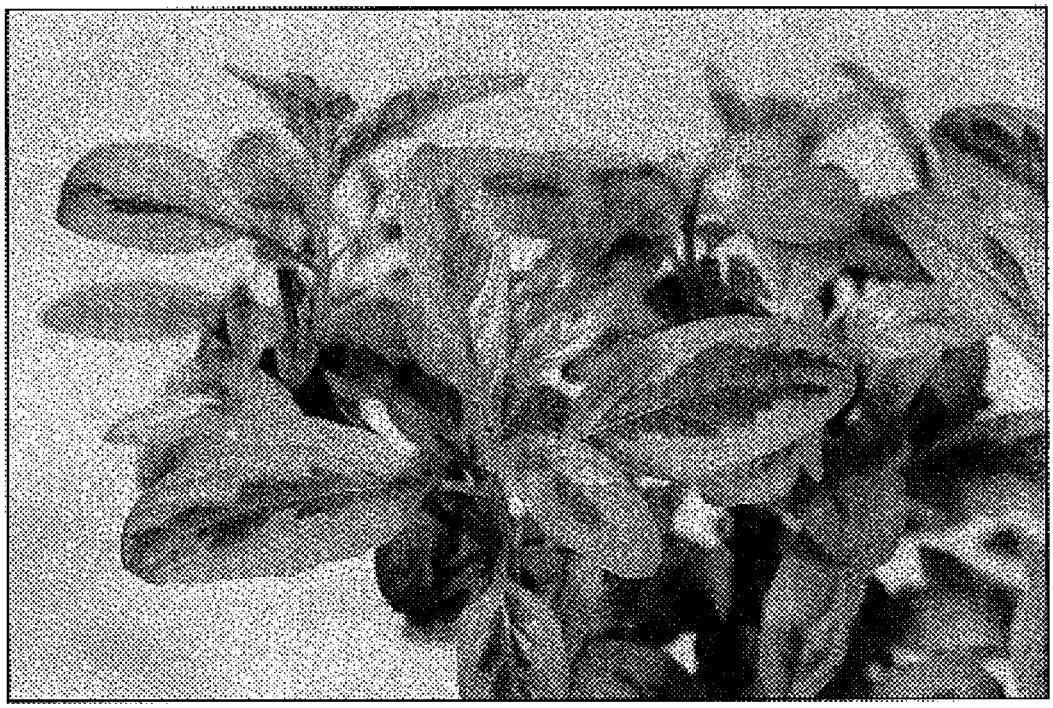

* * * * *